(12) United States Patent
Rebollo Garcia et al.

(10) Patent No.: US 8,957,184 B2
(45) Date of Patent: Feb. 17, 2015

(54) PRO-APOPTOTIC PEPTIDES

(76) Inventors: Angelita Rebollo Garcia, Paris (FR); Alphonse Garcia, Montrouge (FR); Xavier Cayla, Rochecorbon (FR); Issam Arrouss, Charenton le Pont (FR); Katy Billot, Bourg la Reine (FR); Angelique Godet, Paris (FR)

( * ) Notice: Subject to any disclaimer, the term of this patent is extended or adjusted under 35 U.S.C. 154(b) by 405 days.

(21) Appl. No.: 13/262,067

(22) PCT Filed: Mar. 29, 2010

(86) PCT No.: PCT/EP2010/054134
§ 371 (c)(1),
(2), (4) Date: Sep. 29, 2011

(87) PCT Pub. No.: WO2010/112471
PCT Pub. Date: Oct. 7, 2010

(65) Prior Publication Data

US 2012/0021999 A1 Jan. 26, 2012

(30) Foreign Application Priority Data

Mar. 30, 2009 (EP) .................... 09305267

(51) Int. Cl.
*A61K 38/00* (2006.01)
*C07K 14/00* (2006.01)
*C12N 9/64* (2006.01)
*A61P 35/02* (2006.01)

(52) U.S. Cl.
CPC ............... *C12N 9/6475* (2013.01); *A61K 38/00* (2013.01); *C07K 2319/10* (2013.01)

USPC ............................ 530/324; 514/19.6; 514/1.1

(58) Field of Classification Search
None
See application file for complete search history.

(56) References Cited

U.S. PATENT DOCUMENTS

2013/0303439 A1* 11/2013 Rebollo Garcia et al. ..... 514/4.4

FOREIGN PATENT DOCUMENTS

| WO | WO03011898 | * | 2/2003 | ............. C07K 14/16 |
| WO | WO 2004/011595 | | 2/2004 | |
| WO | WO2004011595 | * | 2/2004 | ............. C12N 15/87 |

OTHER PUBLICATIONS

Guergnon et al. Use of penetrating peptides interacting with PP1/PP2A proteins as a basis for a new Drug Phosphatase Technology. Mol. Pharmacol. (2006) 69:1115-1124.*
Ramesh et al. "Protein Phosphatase 2A Regulates Apoptosis in Intestinal Epithelial Cells" The Journal of Biological Chemist 280:35 31091-31100, 2005.*
Guergnon et al. "Use of Penetrating Peptides Interacting with PP1/PP2A Proteins as a General Approach for a Dug Phosphatase Technology", Molecular Pharmacology 69:4 1115-1124, 2006.
Ramesh et al. "Protein Phosphatase 2A Regulates Apoptosis in Intestinal Epithelial Cells" The Journal of Biological Chemistry 280:35 31091-31100, 2005.

* cited by examiner

*Primary Examiner* — Maury Audet
(74) *Attorney, Agent, or Firm* — Cesari and McKenna, LLP (57) ABSTRACT

The invention relates to chimeric peptides useful as pro-apoptotic agents, for inhibition of in vitro cell proliferation and for treatment of tumors.

6 Claims, 7 Drawing Sheets

T, NK, Monocytes

PRO-APOPTOTIC PEPTIDES

The invention relates to pro-apoptotic chimeric peptides.

CROSS REFERENCE TO RELATED APPLICATIONS

This application is the national stage entry under 35 USC 371 for PCT/EP2010/0054134, filed Mar. 29, 2010, which claims the benefit of the Mar. 30, 2009 priority date of European application 09 305267.8.

BACKGROUND OF THE INVENTION

Apoptosis is a regulated process important for differentiation, control of cell number and removal of damaged cells. Failure to regulate apoptosis is a common feature in several diseases, including autoimmune disorders, neurodegenerative diseases and cancer. Apoptosis occurs through the activation of a cell-intrinsic suicide programme and is carried out by internal as well as external signals. The process of apoptosis can be divided in various phases that, at the end, activate signals leading to cell destruction. Although apoptosis is induced by a wide range of death stimuli, the execution phase of apoptosis is carried out, among others, by the caspases, that cleave target proteins leading to cell morphological changes.

Phosphorylation plays a critical role in the regulation of cell physiology and dysregulation of the mechanisms contributes to many disease states. Although much is known regarding alterations in kinase function in diseases such as cancer, the role of specific phosphatases in these same processes remains less characterized. Serine/threonine phosphatases are usually classified as type 1 (PP1) or type 2 (PP2), depending on their substrate specificity and sensitivity to inhibitors. PP1 represents a family of holoenzymes generated by specific interactions between catalytic subunits and a wide variety of regulatory or targeting subunits. PP1 is a major eukaryotic phosphatase that regulates diverse cellular processes such as cell cycle progression, proliferation, protein synthesis, muscle contraction, carbohydrate metabolism, transcription, cytokinesis and neuronal signalling. During cell cycle, PP1 activity is regulated by phosphorylation. PP1 plays a key role in the mitotic transition by dephosphorylating proteins that are essential in these cellular functions. It has been shown that phosphorylation of PP1α at threonine 320 by cyclin-dependent kinases inhibits its enzymatic activity. In agreement, a constitutive mutant of PP1α that is resistant to cdk phosphorylation prevents cells from entering the S phase of cell cycle. Furthermore it was shown that IL-2 deprivation-induced apoptosis operates by regulating Bad dephosphorylation through the PP1α phosphatase (Ayllon et al., 2000) and that PP1α associates to caspase-9 to induce its dephosphorylation and, as a consequence, its protease activity (Dessauge et al., 2006).

Serine/threonine protein phosphatase 2A (PP2A) refers to a large family of dimeric or trimeric enzymes. The PP2A core enzyme consists of a catalytic C subunit (PP2Ac) and a structural A subunit. A third subunit (B) eventually binds to the core and these B subunits regulate both the substrate specificity and localization of PP2A holoenzymes. The A subunit primary serves a structural role and single amino acid alterations disrupt the binding of specific B subunits, suggesting that the A subunit regulates PP2A holoenzyme composition. Various PP2A complexes have been implicated in the control of a variety of cellular processes, including cell proliferation, survival, adhesion, cytoskeletal dynamics and malignant transformation.

A role of PP2A in apoptosis is suggested by its interaction with caspase-3, Bcl-2 and adenovirus E4orf4 protein. The activity of Bcl-2, an anti-apoptotic protein, is regulated by phosphorylation on Ser70, which is required for its anti-apoptotic role and can be reversed by PP2A. Moreover, IL-3 or bryostatin-1-induced phosphorylation of Bcl-2 on Ser70 is followed by increased association between Bcl-2 and PP2A prior to dephosphorylation of Bcl-2. Finally, PP2A regulates apoptosis via modulation of apoptotic signals such as NFkB, ERK and PI3K signalling pathways.

Penetrating peptides interacting with PP1/PP2A proteins were designed. This approach, named "Drug Phosphatase Technology" (DPT), was described in Guergnon et al, 2006 and International patent applications WO2003/011898 and WO2004/011595.

SUMMARY OF THE INVENTION

The invention provides a peptide comprising, or consisting of, the following amino acid sequence (I):

(SEQ ID NO: 1)
(I) X1-KKKIKREI-X2-X3-Y-X4-ETLDGI-X5-EQWA-X6-S-X7

Wherein X1 is vacant, is a lysine residue, or valine-lysine;
X2 is vacant, is a lysine residue, or lysine-isoleucine;
X3 is vacant or is an amino acid sequence of one to 4 amino acids;
X4 is valine or isoleucine;
X5 is phenylalanine or leucine;
X6 is arginine or histidine;
X7 is vacant or is glutamate, or glutamate-aspartate, or glutamate-aspartate-leucine.

In a preferred embodiment, the peptide is VKKK-KIKREIKI-YVETLDGIFEQWAHSEDL (SEQ ID NO:2), also designated "DPT-C9h" in the present disclosure.

Also encompassed are proteolysis-resistant peptides deriving from sequence (I) by one or more chemical modifications, or substantially homologous peptides deriving from sequence (I) by one or more conservative substitutions.

A further subject of the invention is a pharmaceutical composition comprising a peptide as herein described, in association with a pharmaceutically acceptable carrier.

DETAILED DESCRIPTION OF THE INVENTION

The inventors have now shown that PP2A interacts with PP1a/caspase-9 building a trimolecular complex. The inventors found that a particular sequence from the c-terminal portion of caspase-9 protein is a PP2Ac binding domain. When fused to a penetrating peptide with interact with PP1-PP2A, it becomes a therapeutic molecule able to deregulate survival of human cells.

On this basis, the invention provides pro-apoptotic chimeric peptides.

DEFINITIONS

The term "patient" refers to a human or non human animal, preferably a mammal, including male, female, adult and children in need of a treatment wherein a pro-apoptotic effect is desired.

As used herein, the term "treatment" or "therapy" includes curative and/or prophylactic treatment. More particularly, curative treatment refers to any of the alleviation, amelioration and/or elimination, reduction and/or stabilization (e.g., failure to progress to more advanced stages) of a symptom, as well as delay in progression of a symptom of a particular disorder.

Prophylactic treatment refers to any of: halting the onset, reducing the risk of development, reducing the incidence, delaying the onset, reducing the development, as well as increasing the time to onset of symptoms of a particular disorder.

The term "conservative substitution" as used herein denotes the replacement of an amino acid residue by another, without altering the overall conformation and function of the peptide, including, but not limited to, replacement of an amino acid with one having similar properties (such as, for example, polarity, hydrogen bonding potential, acidic, basic, shape, hydrophobic, aromatic, and the like). Amino acids with similar properties are well known in the art. For example, arginine, histidine and lysine are hydrophilic-basic amino acids and may be interchangeable. Similarly, isoleucine, a hydrophobic amino acid, may be replaced with leucine, methionine or valine. Neutral hydrophilic amino acids, which can be substituted for one another, include asparagine, glutamine, serine and threonine. By "substituted" or "modified" the present invention includes those amino acids that have been altered or modified from naturally occurring amino acids.

As such, it should be understood that in the context of the present invention, a conservative substitution is recognized in the art as a substitution of one amino acid for another amino acid that has similar properties. Examples of conservative substitutions are set out in the Table 1 below:

TABLE 1

Conservative Substitutions I

| SIDE CHAIN CHARACTERISTIC | AMINO ACID |
| --- | --- |
| Non-polar | G A P I L V |
| Polar-uncharged | C S T M N Q |
| Polar-charged | D E K R |
| Aromatic | H F W Y |
| Other | N Q D E |

Alternatively, conservative amino acids can be grouped as described in Lehninger, 1975, as set out in Table 2, immediately below.

TABLE 2

Conservative Substitutions II

| SIDE CHAIN CHARACTERISTIC | AMINO ACID |
| --- | --- |
| Non-polar (hydrophobic) | |
| A. Aliphatic: | A L I V P |
| B. Aromatic: | F W |
| C. Sulfur-containing: | M |
| D. Borderline: | G |
| Uncharged-polar | |
| A. Hydroxyl: | S T Y |
| B. Amides: | N Q |
| C. Sulfhydryl: | C |

TABLE 2-continued

Conservative Substitutions II

| SIDE CHAIN CHARACTERISTIC | AMINO ACID |
| --- | --- |
| D. Borderline: | G |
| Positively Charged (Basic): | K R H |
| Negatively Charged (Acidic): | D E |

As still another alternative, exemplary conservative substitutions are set out in Table 3, immediately below.

TABLE 3

Conservative Substitutions III

| Original Residue | Exemplary Substitution |
| --- | --- |
| Ala (A) | Val (V), Leu (L), Ile (I) |
| Arg (R) | Lys (K), Gln (Q), Asn (N) |
| Asn (N) | Gln (Q), His (H), Lys (K), Arg (R) |
| Asp (D) | Glu (E) |
| Cys (C) | Ser (S) |
| Gln (Q) | Asn (N) |
| Glu (E) | Asp (D) |
| His (H) | Asn (N), Gln (Q), Lys (K), Arg (R) |
| Ile (I) | Leu (L), Val (V), Met (M), Ala (A), Phe (F) |
| Leu (L) | Ile (I), Val (V), Met (M), Ala (A), Phe (F) |
| Lys (K) | Arg (R), Gln (Q), Asn (N) |
| Met (M) | Leu (L), Phe (F), Ile (I) |
| Phe (F) | Leu (L), Val (V), Ile (I), Ala (A) |
| Pro (P) | Gly (G) |
| Ser (S) | Thr (T) |
| Thr (T) | Ser (S) |
| Trp (W) | Tyr (T) |
| Tyr (Y) | Trp (W), Phe (F), Thr (T), Ser (S) |
| Val (V) | Ile (I), Leu (L), Met (M), Phe (F), Ala (A) |

Peptide Preparation:

Peptides described herein can be synthesized using standard synthetic methods known to those skilled in the art, for example chemical synthesis or genetic recombination. In a preferred embodiment, peptides are obtained by stepwise condensation of amino acid residues, either by condensation of a preformed fragment already containing an amino acid sequence in appropriate order, or by condensation of several fragments previously prepared, while protecting the amino acid functional groups except those involved in peptide bond during condensation. In particular, the peptides can be synthesized according to the method originally described by Merrifield.

Peptide Characteristics:

The peptides useful in the invention are synthetic peptides deriving from a chimeric synthetic sequence consisting of a penetrating peptide linked to a fragment of caspase-9 protein.

According to one embodiment, peptides useful in the invention comprise, or consist in the following amino acid sequence:

(SEQ ID NO: 1)
(I) X1-KIKIKREI-X2-X3-Y-X4-ETLDGI-X5-EQWA-X6-S-X7

Wherein X1 is vacant, is a lysine residue, or valine-lysine;
X2 is vacant, is a lysine residue, or lysine-isoleucine;
X3 is vacant or is an amino acid sequence of one to 4 amino acids;
X4 is valine or isoleucine;
X5 is phenylalanine or leucine;
X6 is arginine or histidine;

X7 is vacant or is glutamate, or glutamate-aspartate, or glutamate-aspartate-leucine.

When X3 is an amino acid sequence of one to 4 amino acids, it is most preferred that X3 does not react or bind with any native protein or antibody once the peptide is administered to a patient.

In a Preferred Embodiment,
X1 is valine lysine;
X2 is lysine-isoleucine;
and X3 is vacant.

In Another Preferred Embodiment,
X4 is vane:
X5 is phenylalanine;
and X6 is histidine.

A preferred peptide is

```
VKKKKIKREIKI-YVETLDGIFEQWAHSEDL,    (SEQ ID NO: 2)
or
VKKKKIKREIKI-YIETLDGILEQWARSEDL     (SEQ ID NO: 3)
```

The N- and C-termini of the peptides described herein may be optionally protected against proteolysis. For instance, the N-terminus may be in the form of an acetyl group, and/or the C-terminus may be in the form of an amide group. Internal modifications of the peptides to be resistant to proteolysis are also envisioned, e.g. wherein at least a —CONH-peptide bond is modified and replaced by a (CH2NH) reduced bond, a (NHCO) retro-inverso bond, a (CH2-O) methylene-oxy bond, a (CH2-S) thiomethylene bond, a (CH2CH2) carba bond, a (CO—CH2) cetomethylene bond, a (CHOH—CH2) hydroxyethylene bond), a (N—N) bound, a E-alcene bond or also a —CH=CH-bond. The peptides of the invention may be composed of amino acid(s) in D configuration, which render the peptides resistant to proteolysis. They may also be stabilized by intramolecular crosslinking, e.g. by modifying at least two amino acid residues with olefinic side chains, preferably C3-C8 alkenyl chains, preferably penten-2-yl chains) followed by chemical crosslinking of the chains, according to the so-called "staple" technology described in Walensky et al, Science, 2004, 305:1466-1470. For instance, amino acids at position i and i+4 to i+7 can be substituted by non-natural aminoacids that show reactive olefinic residues. All these proteolysis-resistant chemically-modified peptides are encompassed in the present invention.

Also encompassed are substantially homologous peptides deriving from sequence (I) by one or more conservative substitutions. Preferably, these homologous peptides do not include two cysteine residues, so that cyclization is prevented. Two amino acid sequences are "substantially homologous" or "substantially similar" when one or more amino acid residue are replaced by, a biologically similar residue or when greater than 80% of the amino acids are identical, or greater than about 90%, preferably greater than about 95%, are similar (functionally identical). Preferably, the similar or homologous sequences are identified by alignment using, for example, the GCG (Genetics Computer Group, Program Manual for the GCG Package, *Version* 7, Madison, Wis.) pileup program, or any of the programs known in the art (BLAST, FASTA, etc.).

In another aspect of the invention, peptides are covalently bound to a polyethylene glycol (PEG) molecule by their C-terminal terminus or a lysine residue, notably a PEG of 1500 or 4000 MW, for a decrease in urinary clearance and in therapeutic doses used and for an increase of the half-life in blood plasma. In yet another embodiment, peptide half-life is increased by including the peptide in a biodegradable and biocompatible polymer material for drug delivery system forming microspheres. Polymers and copolymers are, for instance, poly(D,L-lactide-co-glycolide) (PLGA) (as illustrated in US2007/0184015, SoonKap Hahn et al).

The peptides as defined herein are useful for inhibition of cell proliferation in vitro.

They are also useful therapeutic agents.

The peptides are useful for the treatment of a tumor, in particular a cancer tumor, preferably in a human patient.

Different types of cancers may include, but are not limited to fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, lymphoma, leukemia, squamous cell carcinoma, basal cell carcinoma, adenocarcinoma, sweat gland carcinoma, sebaceous gland carcinoma, papillary carcinoma, papillary adenocarcinoma, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, and retinoblastoma.

More particularly the peptides described herein are useful in the treatment of cancers which exhibit a deregulation of PP1 and/or PP2A or which exhibit an over-expression of the anti-apoptotic protein Bcl-2, an apoptotic regulator that interacts with and is controlled by PP1 and PP2A.

High levels of expression of the human bcl-2 gene have been found in all lymphomas with t (14; 18) chromosomal translocations including most follicular B cell lymphomas and many large cell non-Hodgkin's lymphomas. High levels of expression of the bcl-2 gene have also been found in leukemias that do not have a t(14; 18) chromosomal translocation, including lymphocytic leukemias of the pre-B cell type, neuroblastomas, nasophryngeal carcinomas, and many adenocarcinomas of the prostate, breast, and colon. Especially overexpression of Bcl-2 was found in chronic lymphocytic leukemia (CLL) (Deng et al, 2009; Prickett et al, 2004).

In a preferred embodiment, the cancer tumor is thus a lymphoma, especially a leukemia, such as chronic lymphocytic leukemia (CLL).

Furthermore, peptides may be used for the treatment of metastases.

Pharmaceutical Compositions:

The peptide may be administered by any convenient route including intravenous, oral, transdermal, subcutaneous, mucosal, intramuscular, intrapulmonary, intranasal, parenteral, rectal, vaginal and topical. Intranasal route is of particular interest.

Advantageously, intra-tumoral administration is also contemplated.

The peptide is formulated in association with a pharmaceutically acceptable carrier.

The dosing is selected by the skilled person so that a pro-apoptotic effect is achieved, and depends on the route of administration and the dosage form that is used Further aspects and advantages of the present invention will be disclosed in the following experimental section, which should be regarded as illustrative and not limiting the scope of the present application.

LEGENDS TO THE FIGURES

Control streptavidin-sepharose alone or conjugated to DPT-C9, DPT-C9r, DPT-sh1 or C9 peptides were incubated with IL-2-stimulated cellular extracts form TS1αβ cells ($10^7$ cells/point). Identification of unbound proteins in lysates or bound proteins in pull-down experiments was performed by immunoblotting using antibodies against PP2Ac or PP1c.

IL-2-stimulated TS1αβ cells cultured 6 h in absence or in presence of DPT-C9, DPT-C9r, DPT-sh1 or C9 peptides were incubated in culture medium at 150 μM for 4 h at 37° C. and stained 4 h with Annexin V and propidium iodide and analyzed by flow cytometry. SD is shown for n=3.

Murine IL-2-stimulated cells were cultured in absence or in presence of DPT-C9h, or C9h peptides (150 μM for 4 h at 37° C.) and then transferred to culture medium with or without IL-2. Human cells were cultured in absence or in presence of DPT-C9h, or C9h peptides (150 μM for 4 h at 37° C.) prior apoptotic analysis. SD is shown for n=3.

PBMC (Peripheral Blood Mononuclear Cell) were isolated by Ficoll gradient centrifugation from healthy donors and CLL patients, cultured in complete RPMI medium and treated with 150 μM of DPT-C9h peptide. Upon 3 h of treatment, cells were washed and resuspended in complete RPMI medium. Apoptosis was estimated 6 h after washing using Annexin staining and specific markers for B cells (FIG. 4A), and for T, NK and monocytes (FIG. 4B). Apoptosis is represented as the percentage compared to cells treated with C9h peptide.

PBMC were isolated by Ficoll gradient centrifugation from healthy donors and three different types of CLL patients: treated, non-treated and resistant. Cells were maintained in complete RPMI medium, treated with 150 μM of DPT-C9h peptide for 3 h and then washed and transferred to complete medium. Samples were analyzed at different times after washing. Apoptosis was estimated by annexin staining. The different populations were selected using specific markers. Apoptosis is represented as percentage compared to control non treated cells.

Mononuclear cells from bone marrow were isolated by Ficoll gradient centrifugation from healthy donors and CLL patients. Cells were treated as in FIG. 5 and apoptosis was estimated by annexin staining. Apoptosis is represented as the percentage compared to control non-treated cells.

PBMC were isolated and treated as in FIG. 5. Upon 30 h, 150 μM of DPT-C9h peptide was re-added to the culture for 3 h and apoptosis was estimated. The different cell populations were selected using specific B markers (FIG. 7A) and using specific T, NK and monocytes markers (FIG. 7B). Apoptosis was compared to control non treated cells.

Cells were cultured in RPMI complete medium with 150 μM of peptide for 3 h. Then, cells were washed and resuspended in complete medium and apoptosis estimated at different times. MCF7 human breast cancer cell line was included as control. Apoptosis is represented as the percentage compared to control non treated cells.

EXAMPLES

Example 1

Identification of Pro-Apoptotic Peptides

Materials
Cells

The following cells were used in this work.

TS1αβ is a murine T cell line stably transfected with the α and β chains of the human IL-2 receptor that can be propagated independently in the presence of IL-2, IL-4 or IL-9 (Pitton et al, 193).

CTLL is a murine T cell line depending on IL-2 for proliferation. CTLL was cultured in RPMI-1640 supplemented with 5% heat-inactivated foetal calf serum, 10 mM Hepes, 2 mM glutamine and 5 ng/ml of rIL-2.

Jurkat and Daudi cells were cultured in RPMI-1640 supplemented with 5% heat-inactivated foetal calf serum, 10 mM Hepes and 2 mM glutamine.

HeLa cells were cultured in DMEM supplemented with 10% heat-inactivated foetal calf serum, 10 mM Hepes and 2 mM glutamine.

Lymphokines, Antibodies, Kits and Reagents

Human rIL-2 was provided by Chiron (Paris, France). Anti-caspase-9 antibody was from Neo markers and anti-protein phosphatase 1 (PP1c) antibody was from Santa Cruz, Calbiochem or Transduction Laboratories. Polyclonal PP2A antibodies used in apoptotic studies were previously described (Ayllón et al, 2000). Annexin V-FITC was from (Beckman Coulter) Immunotech (Marseille, France). Peroxidase (PO)-conjugated goat anti-rabbit, -mouse, or -guinea pig Ig antibody were from Dako (Glostrup, Denmark).

Peptides

Peptides were synthesized in an automated multiple peptide synthesizer with solid phase procedure and standard Fmoc chemistry. The purity and composition of the peptides were confirmed by reverse phase HPLC and by amino acid analysis.

Methods
Peptide Synthesis and Sequence

NH2-biotinylated peptides were synthesized in an automated multiple peptide synthesizer with solid phase procedure and standard Fmoc chemistry. The purity and composition of the peptides were confirmed by reverse phase HPLC and by amino acid analysis. The peptides were used for protein-protein interaction competition studies.

Immobilized Peptide Synthesis

Overlapping peptides covering the whole caspase-9 were prepared by automated spot synthesis into an amino-derivatized cellulose membrane as previously described (Frank and Overwin, 1996; Gausepohl et al., 1992). The membrane was blocked, incubated with PP2Ac (or other PP2A holoenzymes or subunits) and after several washing steps, incubated with anti-PP2Ac antibody followed by the PO-conjugated secondary Ab. Protein interactions were visualized using the ECL system.

Intracellular Detection of Biotinylated Peptides

Exponentially proliferating cells were rinsed twice in PBS. A total of $6\times10^4$ cells per well were seeded in 24 well plates and incubated in RPMI-1640 at 37° C. After 24 h, biotinylated peptides were added and incubated with cells (4 h) for intracellular analysis. Cells were rinsed in PBS and fixed with 0.1% paraformaldehyde (PFA) for 10 min before adding 10 mg/ml of streptavidin-peroxidase. Then, cells were rinsed with PBS, incubated with di-amino-benzidyne (DAB) for 5 min, washed in PBS and analyzed by microscopy.

PP2A-Binding Assays on Cellulose-Bound Peptides Containing Murine Caspase-9 Sequences Overlapping 222 dodecapeptides scanning the whole murine caspase-9 sequence were prepared by automated spot synthesis (Abimed, Langerfeld, Germany) onto an amino-derived cellulose membrane, as described in Frank et al, 1993. The membrane was saturated using SuperBlock (Pierce), incubated with purified PP2Ac subunit and after several washing steps, incubated with anti-PP2Ac antibody, followed by PO-conjugated secondary antibody. Positive spots were visualized using the ECL system.

Pull Down Assays to Determine Interaction of Biotinylated Peptides with Intracellular Protein Targets Biotinylated peptides were preincubated 2 h at 0-100 µM (in final concentration with lysate) at room temperature with 30 µl of streptavidin-coated immunomagnetic beads (Calbiochem, San Diego Calif.). During this time, $10^7$ exponentially growing TS1αβ cells were first washed twice with PBS and then lysed 10 minutes on ice in 400 µl of lysis buffer (50 mM Tris pH7.4, 150 mM NaCl, 20% glycerol, 1% NP-40, 10 mM EDTA, 1 mM PhenylMethylSulfonyl Fluoride, 10 mM NaF, 1 mM orthovanadate, "complete, EDTA-free" protease inhibitor cocktail from Roche).

Lysates were clarified at 13000 g for 10 minutes at 4° C. and were incubated with biotinylated peptides associated with the streptavidin-coated immunomagnetic beads 2 h at 4° C. Biotinylated peptides were pulled down with streptavidin beads and washed two times in 700 µl of lysis buffer on ice. Bound proteins and unbound lysates were then analyzed by SDS-PAGE and Western Blotting using PP1c or PP2Ac antibodies.

Cell Death Assay

The inventors used an Annexin-V-FITC conjugated kit (Roche) for the assessment of outer leaflet exposure of phosphatidylserine (PS) in the plasma membrane of apoptotic cells. Staining was performed according to the manufacturer's instructions. A total of $10^5$ cells were analyzed by flow cytometry in a FACS Calibur cytofluometer (BD Biosciences). Necrotic cells were excluded by propidium iodide (PI) staining, and single annexin V-positive cells were considered apoptotic. For apoptotic analysis the different peptides were used at 150 µM.

Results

In Vitro Identification of Murine Caspase-9 Sequences Involved in PP2Ac Interaction To identify peptides containing caspase-9 sequences able to bind in vitro to PP2Ac, a series of 222 overlapping dodecapeptides from the murine caspase-9 protein (sequence deduced from NCBI accession n° NP_056548) were bound onto a cellulose membrane and incubated with purified PP2Ac subunit. Four peptides with overlapping sequences that bind to a purified catalytic PP2Ac subunit were identified:

```
Peptide 1:          YIETLDGILEQW        (SEQ ID NO: 8)

Peptide 2:           ETLDGILEQWAR       (SEQ ID NO: 9)

Peptide 3:            LDGILEQWARSE      (SEQ ID NO: 10)

Peptide 4:             GILEQWARSEDL     (SEQ ID NO: 11)

PP2Ac Binding     YIETLDGILEQWARSEDL    (SEQ ID NO: 5)
site:
```

Interestingly, while similar results were found when the membrane is incubated with dimeric AC or with trimeric ABaC holoenzyme, no interactive spots were detected with purified A or PP2A-Ba subunits (data not shown). Together these results identified a new PP2Ac binding site corresponding to residues 401-418 of the murine caspase-9 protein (caspase-9 aa 401-418). Furthermore the binding of dimeric AC and trimeric ABaC holoenzymes indicates that binding region on PP2Ac are accessible even in the presence of the regulatory subunits.

Design and Characterization of DPT-C9, a New Penetrating Peptide Containing the Caspase-9 (aa 401-418) PP2Ac Binding Sequence The inventors first chemically synthesized a non cell penetrating peptide named C9 (Table 1) that contains the caspase-9 (aa 401-418) PP2Ac binding domain. In addition, the inventors generated two new DPT-penetrating peptides in order to analyze the intracellular effects of the C9 sequence.

The first penetrating peptide, named DPT-C9, contains the sequence resulting from the fusion of 12 aa residues from DPT-sh1 shuttle and C9 sequence. The second peptide, used as a negative control, contains also a bi-partite sequence resulting from the fusion of DPT-sh1 and C9 reverse sequences. Table 1 illustrates the sequences of these different peptides.

TABLE 1

Sequence of peptides used in this study

| ORIGIN | ACRONYM | SEQUENCE | Cell penetration |
|---|---|---|---|
| CK2α (human) | DPT-sh1 | VKKKKIKREIKI (SEQ ID NO: 4) | Yes |
| Caspase-9 (mouse) | C9 | YIETLDGILEQWARSEDL (SEQ ID NO: 5) | No |
| | DPT-C9 | VKKKKIKREIKI-YIETLDGILEQWARSEDL (SEQ ID NO: 3) | Yes |
| | DPT-C9r | VKKKKIKREIKI-LDESRAWQELIGDLTEIY (SEQ ID NO: 6) | Yes |
| | C9h | YVETLDGIFEQWAHSEDL (SEQ ID NO: 7) | No |
| Caspase-9 (human) | DPT-C9h | VKKKKIKREIKI-YVETLDGIFEQWAHSEDL (SEQ ID NO: 2) | Yes |

Figure 1:
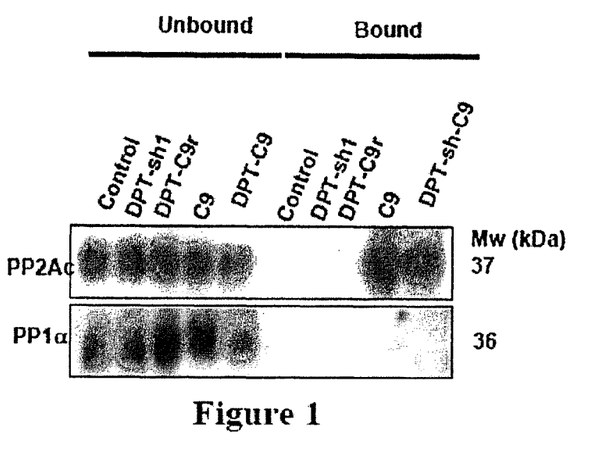
FIG. 1 is an immunoblot that shows interaction of DPT-C9 with PP2Ac.

To determine the capacity of DPT-C9 to interact with PP2Ac, the inventors performed pull-down experiments using cellular extracts from IL-2-stimulated cells incubated with biotinylated peptides or beads alone. The shuttle, DPT-Sh1, as well as the control penetrating peptide Tat (of sequence YGRKKRRQRRR, SEQ ID NO:12) are internalized, as well as the peptides DPT-C9 and DPT-C9r. On the contrary, sequence containing the interaction site of caspase-9 with PP2Ac alone (C9) is not internalized (data not shown). As illustrated in FIG. 1, the inventors found that both C9 and DPT-C9 clearly interact with PP2Ac. In contrast, DPT-sh1 and DPT-C9r do not interact with PP2Ac. The inventors did not detect the presence of PP1c (FIG. 1) or caspase-9 associated to C9 or DPT-C9 (data not shown).

Effect of DPT-C9 on Apoptosis

Figure 2:
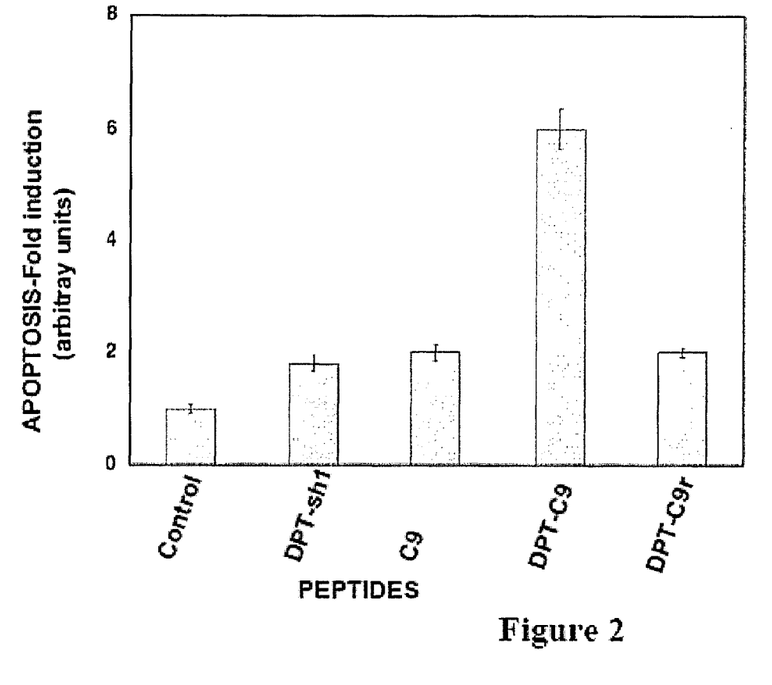
FIG. 2 is a graph that illustrates the effect of DPT-C9 peptide on cell death.

Using flow cytometry detection of Annexin V and PI, the inventors analyzed the capacity of DPT-C9 to induce apoptosis in TS1αβ cells cultured in presence of IL-2. As illustrated on FIG. 2, in contrast to non penetrating C9 peptide, DPT-C9 induced a 6-fold increase of apoptosis. As expected the DPT-sh1 shuttle or DPT-C9r behaves as negative control. Together these results indicate that DPT-C9 induces cell death in murine TS1αβ lymphocytes.

Effect of DPT-C9h on Apoptosis

Figure 3:
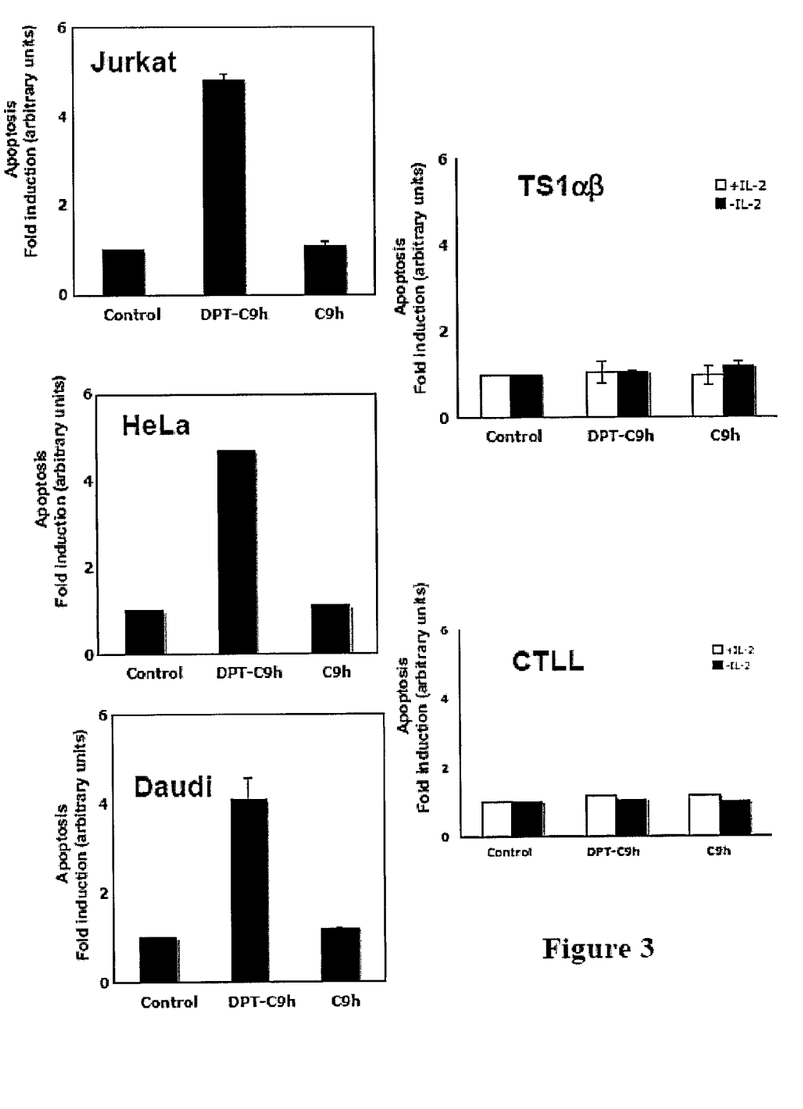
FIG. 3 is a series of graphs that show the effect of DPT-C9h peptide on cell death.

As illustrated on FIG. 3, DPT-C9h, the homolog of human C9 sequence, induced a 5-fold increase of apoptosis in Jurkat, Daudi and HeLa human cells. Interestingly, in contrast to DPT-C9, DPT-C9h is unable to cause cell death in murine TS1αβ or CTLL cell.

Conclusion

The inventors have characterized a new PP2Ac binding sequence, the caspase-9 (aa 401-418) domain, located in the C-terminal portion of the murine caspase-9. The inventors have also identified the homologous PP2Ac binding sequence from human caspase-9 corresponding to the caspase-9 (aa 363-380) domain. Furthermore, by pull-down analysis combined with functional apoptotic studies, the inventors have characterized a new molecule, named DPT-C9, that deregulates survival pathways in TS1αβ lymphocytes. In addition, and in contrast to DPT-C9, DPT-C9h specifically induces cell death in human transformed cell lines with no effect in murine lymphocytes.

DPT-C9 and DPT-C9h are new pro-apoptotic molecules useful for treating a variety of diseases, especially tumors.

Furthermore DPT-C9 and DPT-C9h are molecular tools to isolate PP2Ac and PP2A-associated partners.

It is noteworthy that in cells PP2Ac has never been found as a free molecule. PP2Ac usually binds to a structural subunit (A subunit or PR65). Alternatively, PP2Ac can also bind to mammalian α4, a protein related to yeast Tap42.

Tap42/a4, when phosphorylated by the mTOR kinase, interacts with PP2Ac via a N-terminal ordered helical domain. Furthermore, previous work from Brautigan's Group indicates that basic charged residues of PP2Ac are required for binding to negatively charged residues of PR65/A or a4/Tap42 proteins. Interestingly, the helical structure of C9 domain, deduced from mouse caspase-9, contains several acidic charged (D/E) residues that could generate a negative electrostatic potential also favoring interaction with PP2Ac. A similar situation also potentially occurs with human caspase-9 sequence.

Together these observations suggest that the DPT-C9 and DPT-C9h peptides, containing the C9/C9h sequences, allow identification and easier purification of PP2Ac and associated partners. Based on pull-down assays coupled with proteomic analysis, DPT-C9/DPT-C9h peptides could easily allow isolation and identification of PP2A proteins and PP2A-associated proteins in functional intracellular molecular complexes. This new approach is more specific than usual microcystin-based affinity techniques since they cannot discriminate between PP1 and PP2A proteins. In addition these pull-down strategies allow to determine the phosphatase activities associated to PP2Ac in these complexes.

Example 2

Pre-Clinical Evaluation DPT-C9h

Materials and Methods

Isolation of Cell Populations

Fresh blood from healthy donors was collected by the Etablissement Français du Sang. CLL and bone marrow samples were obtained from the Hematology Service, according to a protocol approved by the institutional ethic committee.

Mononuclear cells isolated from peripheral blood (PBMC) were prepared by Ficoll gradient centrifugation.

T cells were isolated from PBMC using positive selection by anti-CD3 Dynal magnetic beads.

B cells and monocytes were isolated using Dynal negative isolation kit (Invitrogen).

NK cells were isolated using the NK Cell Isolation Kit II (Miltenyi Biotec), an indirect magnetic labelling system for the isolation of untouched NK cells.

The purity of the isolated T, B, monocytes and NK cells reached up to 95%.

Detection of Apoptosis by Annexin Staining

A total of $2.5 \times 10^5$ cells were washed with ice-cold PBS, diluted in ice-cold binding buffer and stained with annexin and propidium iodide (PI). Samples were maintained on ice for 10 min in the dark and then analyzed by flow cytometry.

Peptide Synthesis and Sequence $NH_2$-biotinylated peptides were synthesized in an automated multiple peptide synthesizer with solid phase procedure and standard Fmoc chemistry. The purity and composition of the peptides were confirmed by reverse phase HPLC and by amino acid analysis.

Results

Effect of DPT-C9h Peptide on CCL Patients

Figure 4:
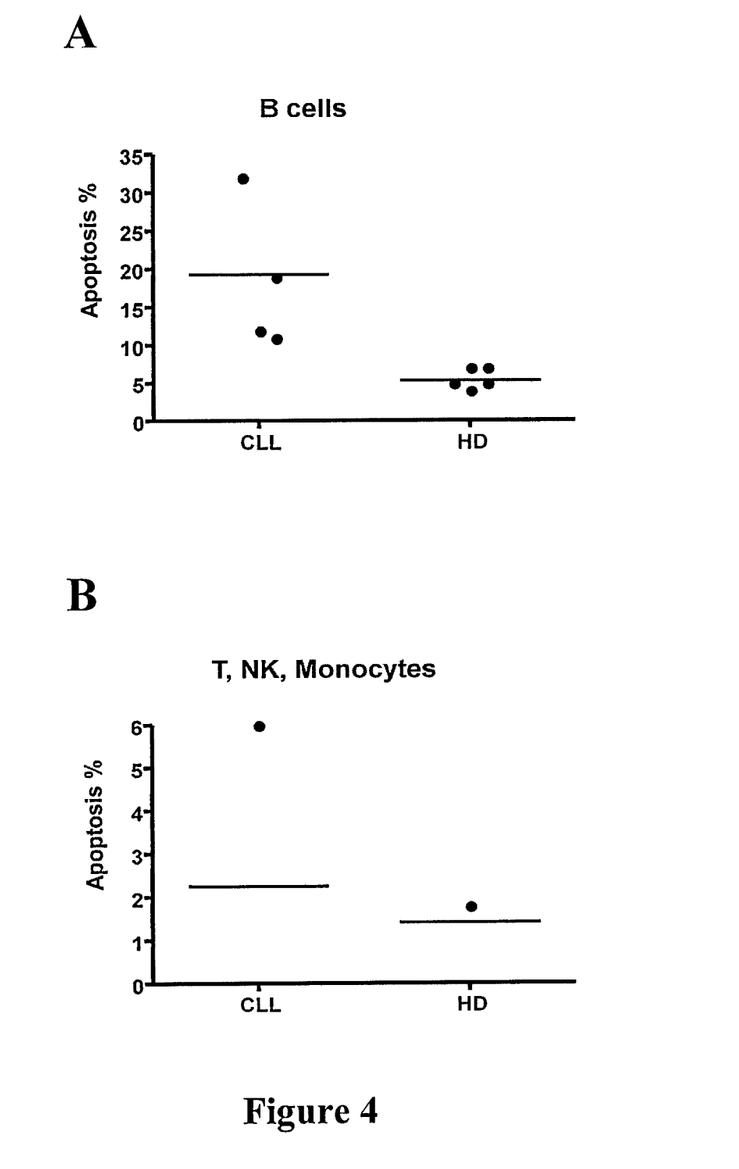
FIG. 4 represents two graphs that illustrate the apoptotic effect of DPT-C9h on CLL (Chronic lymphocityc leukemia) cells compared to HD (Healthy donor) cells.
Figure 5:
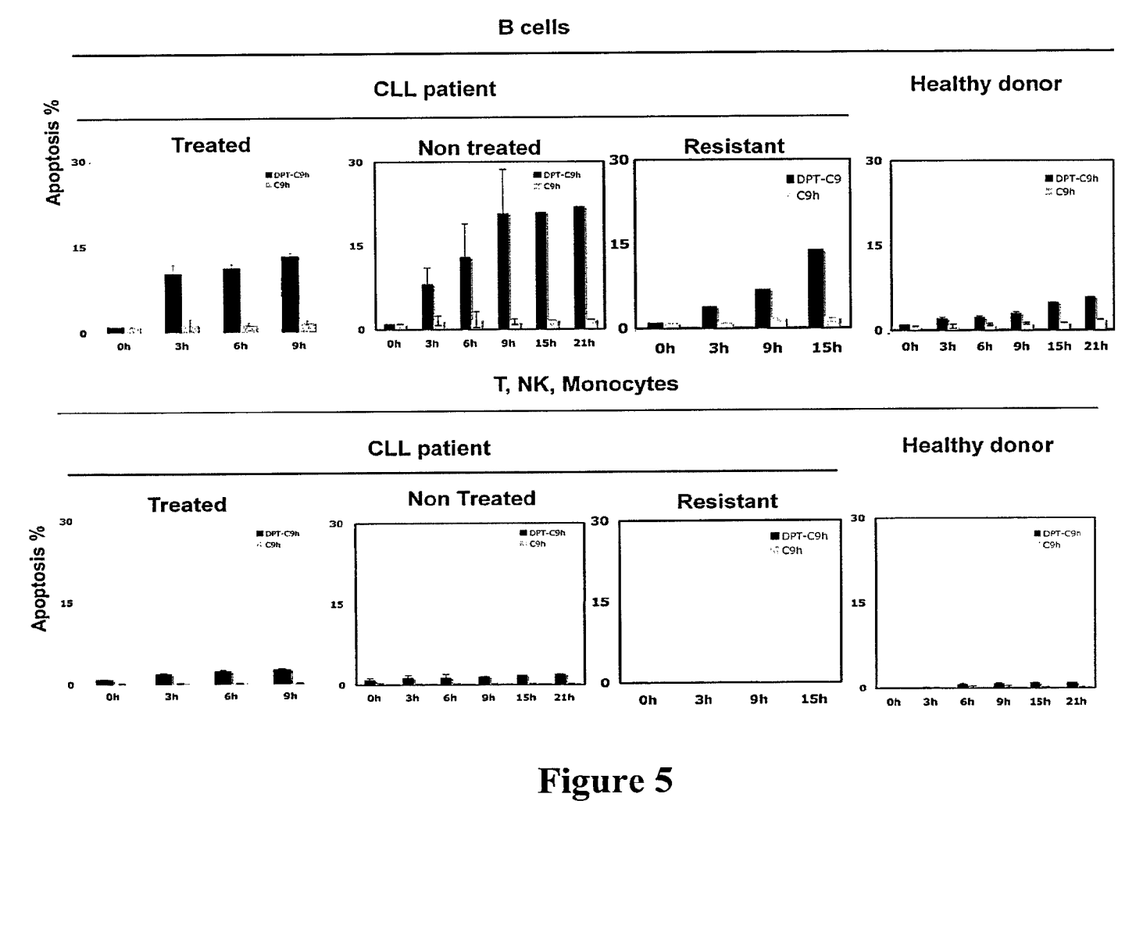
FIG. 5 is a series of graphs that show the effect of DPT-C9h treatment on various CLL patients.

The inventors analyzed the capacity of DPT-C9h to induce apoptosis in PBMC. FIGS. 4 and 5 show that the DPT-C9h peptide, displays penetrating and apoptotic properties in primary B cells from CLL patients but not from healthy donors. Furthermore, the DPT-C9h peptide has no effect neither on human T and NK cells nor on human monocytes.

Effect of DPT-C9h on CLL Patients Resistant

Figure 6:
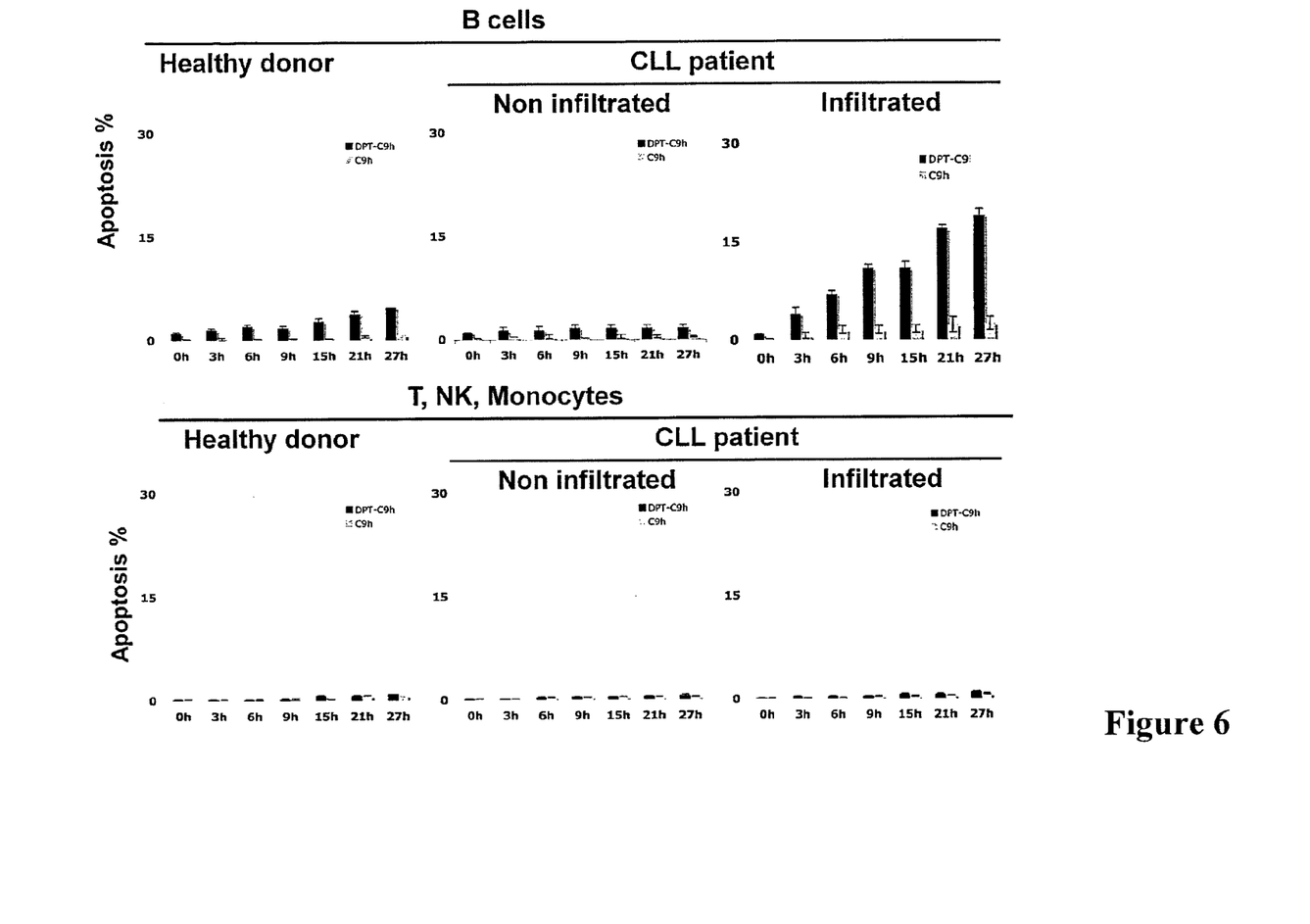
FIG. 6 is a series of graphs that illustrate the effect of DPT-C9h peptide on bone marrow cells.

Interestingly, DPT-C9h is able to induce apoptosis in B cells from CLL patients resistant to classical chemotherapy treatment (FIG. 6). The DPT-C9h peptide has no effect on T and NK cells and monocytes from CLL patients resistant to classical chemotherapy treatment.

Effect of DPT-C9h on Bone Marrow Cells

Figure 7:
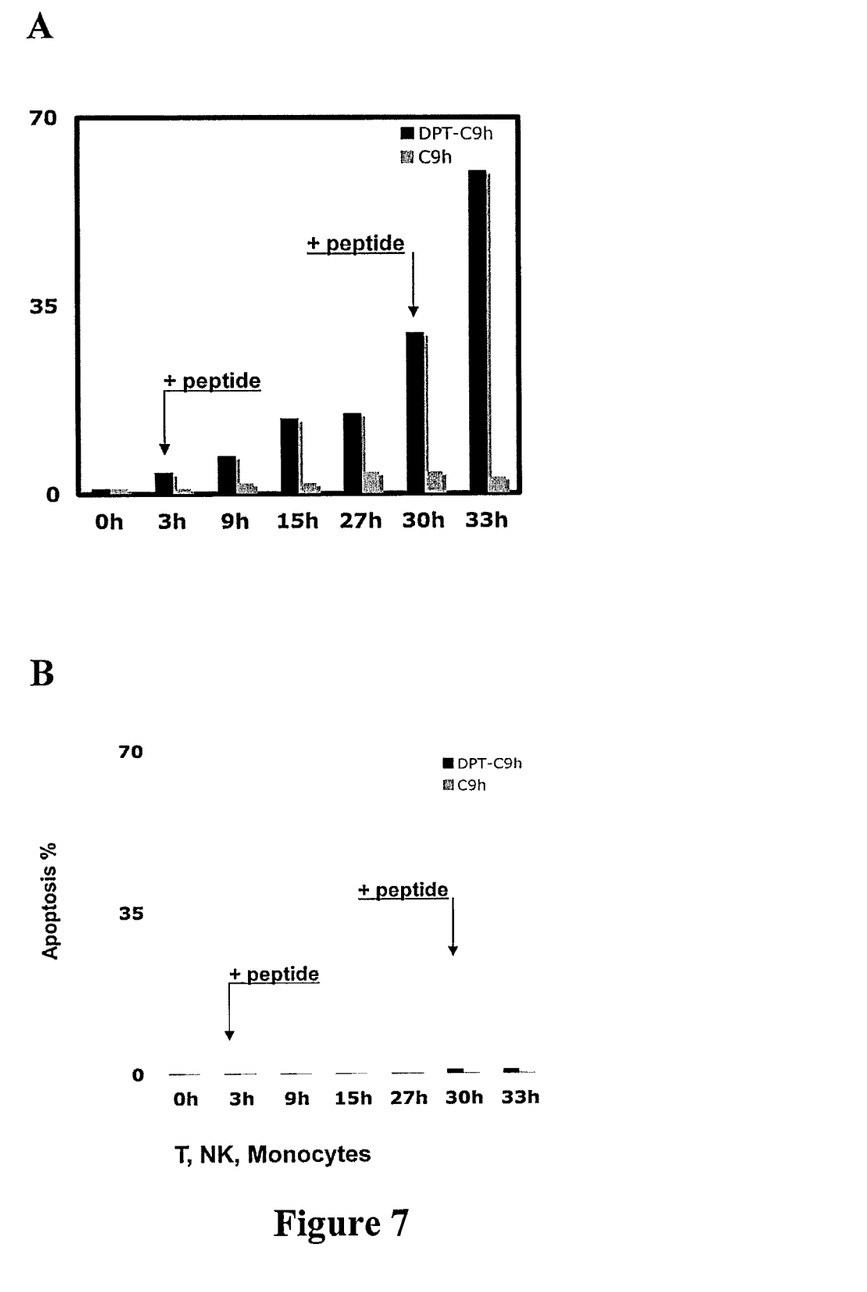
FIG. 7 represents two graphs that show the effect of DPT-C9h treatment on CLL resistant cells.

As illustrated on FIG. 7, DPT-C9h has cell penetrating and apoptotic activity in bone marrow B cells from CLL patients and no effect on bone marrow B cells from healthy donors. The DPT-C9h peptide has no effect on T and NK cells and monocytes neither on bone marrow B cells from CLL patients nor on bone marrow B cells from healthy patients.

Figure 8:
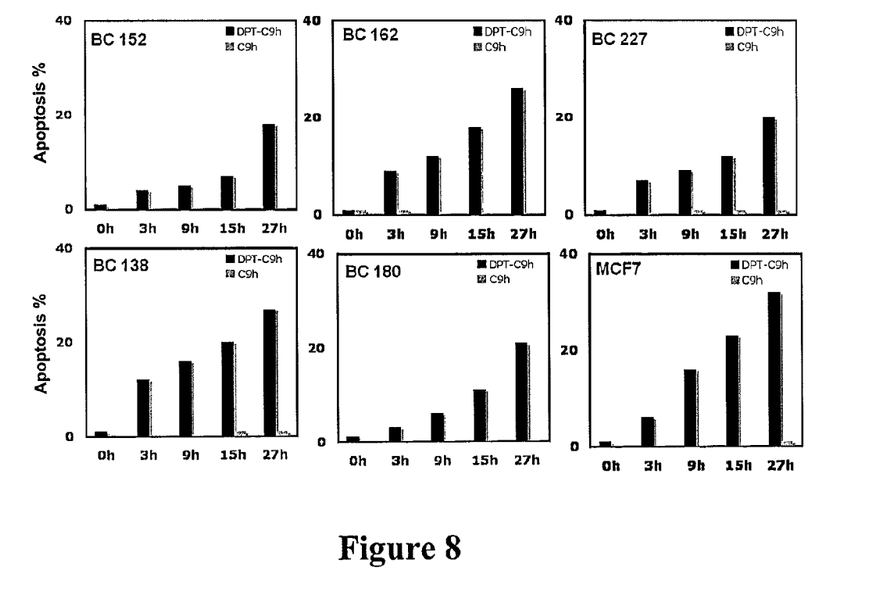
FIG. 8 is a series of graphs that illustrate the effect of DPT-C9h on breast cancer cells isolated from human models of breast cancer xenografts.

Effect of DPT-C9h on In Vivo Human Xenografts of Breast Cancer and on Breast Cancer Cell Line Finally, as shown on FIG. 8, DPT-C9h exhibited dramatic apoptotic effect in cell lines isolated from in vivo human xenografts of breast cancer as well as in the breast cancer cell line MCF7.

Conclusion

The above results show that DPT-C9h is able to discriminate between healthy and tumoral cells. The selective effect of DPT-C9h peptide between healthy donors and CLL patients may be due to the conformational changes of the complex PP1/caspase-9/PP2Ac, probably induced by the association of other partners to the complex.

Finally, DPT-C9h peptide was shown to be stable in culture medium for at least 18 h.

REFERENCES

Ayllón, C. Martinez-A. A. Garcia, X. Cayla, and A. Rebollo (2000). Protein phosphatase 1-a is a Ras-activated Bad phosphatase that regulates IL-2 deprivation-induced apoptosis. EMBO J. 19: 1-10.

Deng X, Gao F, and W. Stratford May. Dephosphorylation and up-regulation of Bcl2-p53 binding Protein phosphatase 2A inactivates Bcl-2's antiapoptotic function by dephosphorylation and up-regulation of Bcl2-p53 binding. Blood. 2009 Jan. 8; 113(2):422-8.

Dessauge, X. Cayla, A. Fleischer, A. Ghadiri, M. Duhamel, and A. Rebollo: Caspase-9-dependent apoptosis is induced by serine/threonine phosphatase PP1a. J. Immunol. 2006. 177, 2441-2451.

Frank, R. and Overwing, H. 1996. Spot synthesis: epitope analysis with arrays of synthetic peptides prepared on cellulose membrane. Meth. Mol. Biol. 66, 149-169.

Gausepohl, H., Boulin, C., Kraft, M. and Frank, R. W. (1992) Automated multiple peptide synthesis. Pept Res, 5, 315-320.

Garcia, X. Cayla, J. Guergnon, F, Dessauge, V, Hospital, M P, Rebollo, A, Fleischer, A. Rebollo. Serine/threonine protein phosphatases PP1 and PP2A are key players in apoptosis. Biochimie. (2003) 85:721-726.

Guergnon, F. Dessauge, V. Dominguez, J. Viallet, X. Cayla, A. Rebollo, V. Yuste, S. Susin, P E. Bost and A. Garcia Use of penetrating peptides interacting with PP1/PP2A proteins as a basis for a new Drug Phosphatase Technology. Mol. Pharmacol. (2006) 69:1115-1124.

Lehninger, (1975) Biochemistry, Second Edition, Worth Publishers, Inc. New-York: NY., pp. 71-77.

Pitton, C., Rebollo, A., Van Snick, J., Theze, J. and Garcia, A. (1993) High affinity and intermediate affinity forms of the human IL-2 receptor expressed in an IL-9-dependent murine T cell line deliver proliferative signals via differences in their transduction pathways. Cytokine, 5, 362-371.

Prickett TD, and Brautigan D (2004). Ovelapping binding sites in Protein Phosphatase 2A for association with regulatory 1 and a4 (mTap42) subunits. J. Biol. Chem. 279, 38912-38920.

The invention claimed is:

1. An isolated peptide comprising the amino acid sequence of SEQ ID NO: 2 or SEQ ID NO: 3 or a proteolysis-resistant derivative thereof including one or more chemical modifications conferring proteolysis resistance to the isolated peptide, wherein the one or more chemical modifications consist of an N-terminal acetyl group or a C-terminal amide group and do not alter the ability of the isolated peptide to bind to the catalytic subunit of protein phosphatase 2A (PP2Ac).

2. The isolated peptide of claim 1, wherein the amino acid sequence is

VKKKKIKREIKIYVETLDGIFEQWAHSEDL (SEQ ID NO: 2).

3. The isolated peptide of claim 1, wherein the amino acid sequence is

VKKKKIKREIKIYIETLDGILEQWARSEDL (SEQ ID NO: 3).

4. A pharmaceutical composition, comprising the isolated peptide as defined in claim 1, with a pharmaceutically acceptable carrier.

5. A pharmaceutical composition, comprising the isolated peptide as defined in claim 2, in association with a pharmaceutically acceptable carrier.

6. A pharmaceutical composition, comprising the isolated peptide as defined in claim 3, in association with a pharmaceutically acceptable carrier.

* * * * *

SEQUENCE LISTING

```
<160> NUMBER OF SEQ ID NOS: 12

<210> SEQ ID NO 1
<211> LENGTH: 27
<212> TYPE: PRT
<213> ORGANISM: artificial sequence
<220> FEATURE:
<223> OTHER INFORMATION: Synthetic polypeptide
<220> FEATURE:
<221> NAME/KEY: MISC_FEATURE
<222> LOCATION: (1)..(1)
<223> OTHER INFORMATION: Xaa is vacant, is a lysine residue, or valine-
      lysine
<220> FEATURE:
<221> NAME/KEY: MISC_FEATURE
<222> LOCATION: (10)..(10)
<223> OTHER INFORMATION: Xaa is vacant, is a lysine residue, or lysine-
      isoleucine
<220> FEATURE:
<221> NAME/KEY: MISC_FEATURE
<222> LOCATION: (11)..(11)
<223> OTHER INFORMATION: Xaa is vacant or is an amino acid sequence of
      one to 4 amino acids
<220> FEATURE:
<221> NAME/KEY: MISC_FEATURE
<222> LOCATION: (13)..(13)
<223> OTHER INFORMATION: Xaa is valine or isoleucine
<220> FEATURE:
<221> NAME/KEY: MISC_FEATURE
<222> LOCATION: (20)..(20)
<223> OTHER INFORMATION: Xaa is phenylalanine or leucine
<220> FEATURE:
<221> NAME/KEY: MISC_FEATURE
```

```
<222> LOCATION: (25)..(25)
<223> OTHER INFORMATION: Xaa is arginine or histidine
<220> FEATURE:
<221> NAME/KEY: MISC_FEATURE
<222> LOCATION: (27)..(27)
<223> OTHER INFORMATION: Xaa is vacant or is glutamate, or glutamate-
      aspartate, or glutamate-aspartate-leucine

<400> SEQUENCE: 1

Xaa Lys Lys Lys Ile Lys Arg Glu Ile Xaa Xaa Tyr Xaa Glu Thr Leu
1               5                   10                  15

Asp Gly Ile Xaa Glu Gln Trp Ala Xaa Ser Xaa
            20                  25

<210> SEQ ID NO 2
<211> LENGTH: 30
<212> TYPE: PRT
<213> ORGANISM: artificial sequence
<220> FEATURE:
<223> OTHER INFORMATION: Synthetic polypeptide

<400> SEQUENCE: 2

Val Lys Lys Lys Lys Ile Lys Arg Glu Ile Lys Ile Tyr Val Glu Thr
1               5                   10                  15

Leu Asp Gly Ile Phe Glu Gln Trp Ala His Ser Glu Asp Leu
            20                  25                  30

<210> SEQ ID NO 3
<211> LENGTH: 30
<212> TYPE: PRT
<213> ORGANISM: artificial sequence
<220> FEATURE:
<223> OTHER INFORMATION: Synthetic polypeptide

<400> SEQUENCE: 3

Val Lys Lys Lys Lys Ile Lys Arg Glu Ile Lys Ile Tyr Ile Glu Thr
1               5                   10                  15

Leu Asp Gly Ile Leu Glu Gln Trp Ala Arg Ser Glu Asp Leu
            20                  25                  30

<210> SEQ ID NO 4
<211> LENGTH: 12
<212> TYPE: PRT
<213> ORGANISM: artificial sequence
<220> FEATURE:
<223> OTHER INFORMATION: Synthetic polypeptide

<400> SEQUENCE: 4

Val Lys Lys Lys Lys Ile Lys Arg Glu Ile Lys Ile
1               5                   10

<210> SEQ ID NO 5
<211> LENGTH: 18
<212> TYPE: PRT
<213> ORGANISM: artificial sequence
<220> FEATURE:
<223> OTHER INFORMATION: Synthetic polypeptide

<400> SEQUENCE: 5

Tyr Ile Glu Thr Leu Asp Gly Ile Leu Glu Gln Trp Ala Arg Ser Glu
1               5                   10                  15

Asp Leu

<210> SEQ ID NO 6
<211> LENGTH: 30
```

-continued

```
<212> TYPE: PRT
<213> ORGANISM: artificial sequence
<220> FEATURE:
<223> OTHER INFORMATION: Synthetic polypeptide

<400> SEQUENCE: 6

Val Lys Lys Lys Ile Lys Arg Glu Ile Lys Ile Leu Asp Glu Ser
1               5                   10                  15

Arg Ala Trp Gln Glu Leu Ile Gly Asp Leu Thr Glu Ile Tyr
            20                  25                  30

<210> SEQ ID NO 7
<211> LENGTH: 18
<212> TYPE: PRT
<213> ORGANISM: artificial sequence
<220> FEATURE:
<223> OTHER INFORMATION: Synthetic polypeptide

<400> SEQUENCE: 7

Tyr Val Glu Thr Leu Asp Gly Ile Phe Glu Gln Trp Ala His Ser Glu
1               5                   10                  15

Asp Leu

<210> SEQ ID NO 8
<211> LENGTH: 12
<212> TYPE: PRT
<213> ORGANISM: artificial sequence
<220> FEATURE:
<223> OTHER INFORMATION: Synthetic polypeptide

<400> SEQUENCE: 8

Tyr Ile Glu Thr Leu Asp Gly Ile Leu Glu Gln Trp
1               5                   10

<210> SEQ ID NO 9
<211> LENGTH: 12
<212> TYPE: PRT
<213> ORGANISM: artificial sequence
<220> FEATURE:
<223> OTHER INFORMATION: Synthetic polypeptide

<400> SEQUENCE: 9

Glu Thr Leu Asp Gly Ile Leu Glu Gln Trp Ala Arg
1               5                   10

<210> SEQ ID NO 10
<211> LENGTH: 12
<212> TYPE: PRT
<213> ORGANISM: artificial sequence
<220> FEATURE:
<223> OTHER INFORMATION: Synthetic polypeptide

<400> SEQUENCE: 10

Leu Asp Gly Ile Leu Glu Gln Trp Ala Arg Ser Glu
1               5                   10

<210> SEQ ID NO 11
<211> LENGTH: 12
<212> TYPE: PRT
<213> ORGANISM: artificial sequence
<220> FEATURE:
<223> OTHER INFORMATION: Synthetic polypeptide

<400> SEQUENCE: 11

Gly Ile Leu Glu Gln Trp Ala Arg Ser Glu Asp Leu
1               5                   10
```

```
<210> SEQ ID NO 12
<211> LENGTH: 11
<212> TYPE: PRT
<213> ORGANISM: artificial sequence
<220> FEATURE:
<223> OTHER INFORMATION: Synthetic polypeptide

<400> SEQUENCE: 12

Tyr Gly Arg Lys Lys Arg Arg Gln Arg Arg Arg
1               5                   10
```